(12) United States Patent
Machida et al.

(10) Patent No.: US 9,085,012 B2
(45) Date of Patent: Jul. 21, 2015

(54) ULTRASONIC TRANSDUCER AND ULTRASONIC DIAGNOSTIC APPARATUS PROVIDED WITH SAME

(75) Inventors: Shuntaro Machida, Kokubunji (JP); Takashi Kobayashi, Higashimurayama (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 809 days.

(21) Appl. No.: 13/321,947

(22) PCT Filed: May 21, 2010

(86) PCT No.: PCT/JP2010/058636
§ 371 (c)(1),
(2), (4) Date: Nov. 22, 2011

(87) PCT Pub. No.: WO2010/137528
PCT Pub. Date: Dec. 2, 2010

(65) Prior Publication Data
US 2012/0069701 A1 Mar. 22, 2012

(30) Foreign Application Priority Data
May 25, 2009 (JP) ................. 2009-124840

(51) Int. Cl.
*B06B 1/02* (2006.01)
*B81B 3/00* (2006.01)
(Continued)

(52) U.S. Cl.
CPC ............ *B06B 1/0292* (2013.01); *B81B 3/0021* (2013.01); *G01N 29/2406* (2013.01); *H04R 19/005* (2013.01); *A61B 8/00* (2013.01); *A61B 8/4483* (2013.01); *B81B 2201/0257* (2013.01)

(58) Field of Classification Search
CPC .................... B81B 3/0021; B81B 2201/0257; B06B 1/0292; A61B 8/4483; A61B 8/4488; H04R 19/005; G01N 29/2406
USPC .......... 600/459; 257/416; 381/175; 310/334; 367/140
See application file for complete search history.

(56) References Cited

U.S. PATENT DOCUMENTS 4,887,248 A * 12/1989 Griebeler ...................... 367/181
6,320,239 B1 11/2001 Eccardt et al.
(Continued)

FOREIGN PATENT DOCUMENTS

| JP | 2002191180 | 7/2002 |
|---|---|---|
| JP | 2003000599 | 1/2003 |

(Continued)

OTHER PUBLICATIONS

International Search Report from International Application No. PCT/JP2010/058636 mailed Jun. 22, 2010.

*Primary Examiner* — Ari M Diacou
(74) *Attorney, Agent, or Firm* — Brundidge & Stanger, P.C.

(57) ABSTRACT

For disposing projections of insulating film protruding into a hollow part in CMUT in order to suppress injection of electrical charge into the insulating film due to contact of a lower surface of a membrane with a lower surface of the hollow part, there are provided a structure of disposed projections preferred for suppressing increase in driving voltage for CMUT and decrease in receiving sensitivity, and an ultrasonic diagnostic apparatus using the same. The ultrasonic transducer of the present invention comprises a first electrode, a lower insulating film formed on the first electrode, an upper insulating film provided so as to form a hollow part above the lower insulating film, and a second electrode formed on the upper insulating film, and is characterized in that the lower insulating film or the upper insulating film has projections on the side of the hollow part, and the first electrode or the second electrode has openings formed at positions corresponding to the positions at which the projections are formed.

15 Claims, 12 Drawing Sheets

(51) Int. Cl.
   *G01N 29/24* (2006.01)
   *H04R 19/00* (2006.01)
   *A61B 8/00* (2006.01)

(56) References Cited

U.S. PATENT DOCUMENTS

| | | | |
|---|---|---|---|
| 6,562,650 | B2 | 5/2003 | Ladabaum |
| 6,571,445 | B2 | 6/2003 | Ladabaum |
| 7,675,221 | B2 * | 3/2010 | Machida et al. ............... 310/322 |
| 8,198,782 | B2 * | 6/2012 | Machida et al. ............... 310/322 |
| 2005/0228285 | A1 | 10/2005 | Huang et al. |
| 2006/0179640 | A1 * | 8/2006 | Machida et al. ............... 29/594 |
| 2006/0238067 | A1 * | 10/2006 | Dausch ........................ 310/311 |
| 2007/0052093 | A1 * | 3/2007 | Machida et al. ............... 257/735 |
| 2007/0180916 | A1 * | 8/2007 | Tian et al. ...................... 73/649 |
| 2007/0264732 | A1 | 11/2007 | Chen |
| 2008/0089180 | A1 * | 4/2008 | Matsumoto et al. ........... 367/181 |
| 2009/0122651 | A1 * | 5/2009 | Kupnik et al. ................. 367/181 |
| 2009/0204001 | A1 * | 8/2009 | Ona et al. ...................... 600/443 |
| 2010/0148594 | A1 * | 6/2010 | Machida et al. ................. 310/10 |
| 2010/0173437 | A1 * | 7/2010 | Wygant et al. ................... 438/53 |
| 2010/0176821 | A1 * | 7/2010 | Kasai et al. .................... 324/660 |
| 2010/0207484 | A1 * | 8/2010 | Chang .......................... 310/300 |
| 2013/0241345 | A1 * | 9/2013 | Takezaki et al. .............. 310/300 |
| 2014/0307528 | A1 * | 10/2014 | Dekker et al. ................. 367/178 |

FOREIGN PATENT DOCUMENTS

| | | |
|---|---|---|
| JP | 2004057460 | 2/2004 |
| JP | 2006-020313 | 1/2006 |
| JP | 2006-211185 | 8/2006 |
| JP | 2007-074263 | 3/2007 |
| JP | 2008-098697 | 4/2008 |
| JP | 2008-099036 | 4/2008 |
| JP | 2009-055474 | 3/2009 |
| JP | 2009-100460 | 5/2009 |

* cited by examiner

Fig. 10
(a)
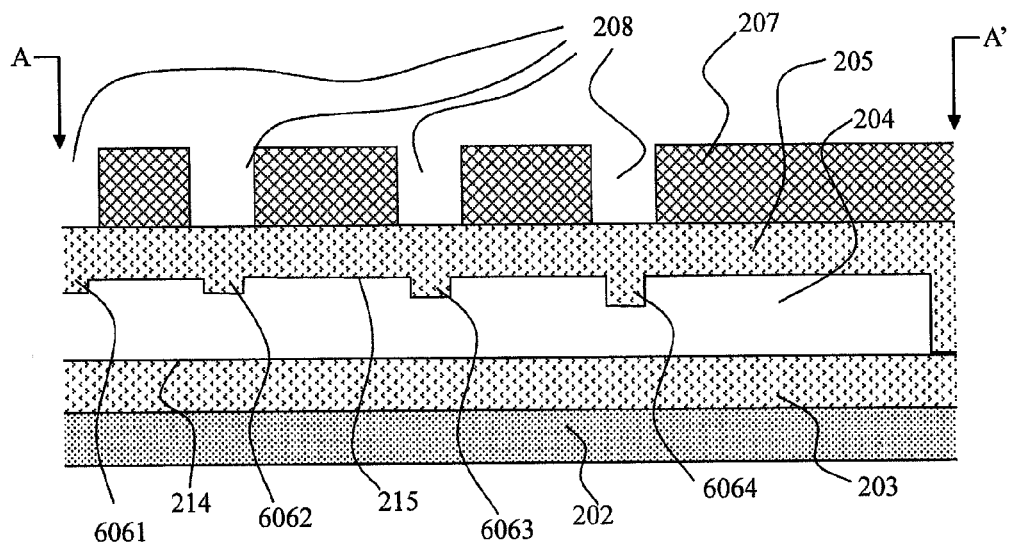
(b)
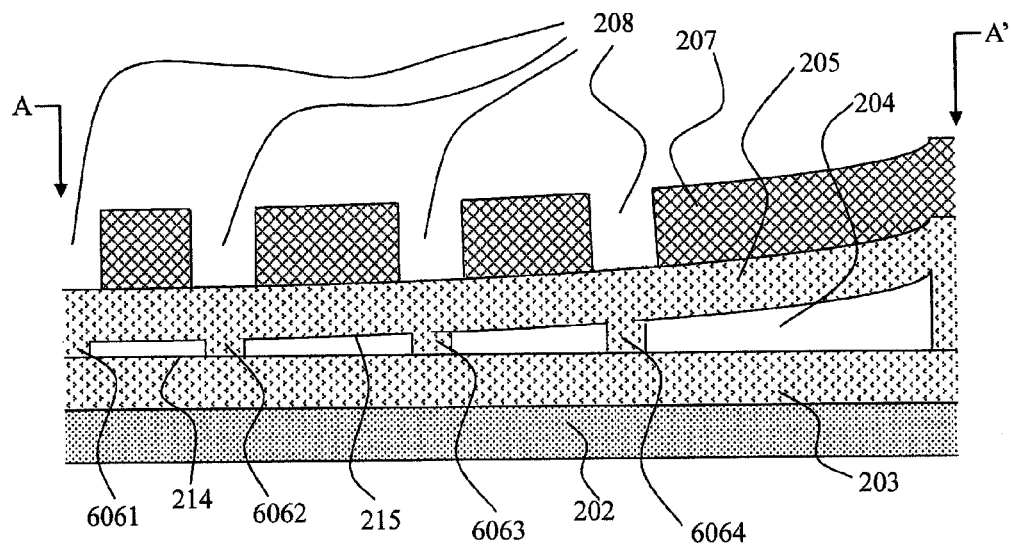

ULTRASONIC TRANSDUCER AND ULTRASONIC DIAGNOSTIC APPARATUS PROVIDED WITH SAME

TECHNICAL FIELD

The present invention relates to an ultrasonic transducer and an ultrasonic diagnostic apparatus using the same. In particular, the present invention relates to an ultrasonic transducer produced by the micro-electro-mechanical system (MEMS) technology, and an ultrasonic diagnostic apparatus using the same.

BACKGROUND ART

Ultrasonic transducers, which transmit and receive ultrasonic waves, are used for apparatuses for diagnosing tumors in human bodies etc., apparatuses for performing nondestructive tests of structures etc.

As the ultrasonic transducers, those utilizing vibration of piezoelectric substances have so far been used. However, with progress of the MEMS technology in recent years, capacitive micromachined ultrasonic transducers (CMUTs) comprising a vibration part formed on a silicon substrate have been developed, and researches are actively conducted aiming at practical use thereof.

For example, U.S. Pat. No. 6,320,239 B2 (Patent document 1) discloses a single CMUT and a CMUT array.

U.S. Pat. No. 6,571,445 B2 (Patent document 2) and U.S. Pat. No. 6,562,650 B2 (Patent document 3) disclose techniques for forming CMUT in an upper layer of a signal processing circuit formed on a silicon substrate.

Further, U.S. Patent Published Application Nos. 2005/0228285 A1 (Patent document 4) and 2007/0264732 A1 (Patent document 5) disclose CMUTs having a structure comprising a projection protruding into a hollow part.

PRIOR ART REFERENCES

Patent Documents

Patent document 1: U.S. Pat. No. 6,320,239 B1
Patent document 2: U.S. Pat. No. 6,571,445 B2
Patent document 3: U.S. Pat. No. 6,562,650 B2
Patent document 4: U.S. Patent Published Application No. 2005/0228285 A1
Patent document 5: U.S. Patent Published Application No. 2007/0264732 A1

SUMMARY OF THE INVENTION

Object to be Achieved by the Invention

In contrast to the conventional transducers utilizing a piezoelectric substance, CMUTs have advantages of the wide frequency band of usable ultrasonic waves, high sensitivity, and so forth. Moreover, since they are produced by using LSI processing techniques, micro processing can be used. In particular, it is considered that, when ultrasonic devices are arranged in the form of array and independently controlled, CMUTs become indispensable. This is because, while wiring for each device is needed and thus the number of the wiring in the array becomes a huge number, CMUTs are produced by using LSI processing techniques, and therefore the wiring is easy. Moreover, that is also because the CMUTs can be embedded on one chip of a circuit which processes signals from an ultrasonic transmission part.

With reference to FIG. 1, fundamental structure and operation of CMUT will be explained. Above a lower electrode 101, a hollow part 102 surrounded by an insulating film 103 is formed. Above the hollow part 102, an upper electrode 104 is disposed via the insulating film 103. If a DC voltage and an AC voltage are superimposed between the upper electrode 104 and the lower electrode 101, an electrostatic force is generated between the upper electrode 104 and the lower electrode 101, and a membrane 105 constituted by the insulating film 103 and the upper electrodes 104 above the hollow part 102 vibrates at the frequency of the applied AC voltage to transmit ultrasonic waves.

In contrast, in the case of reception, the membrane 105 is vibrated by pressure of ultrasonic waves that arrive at the surface of the membrane 105. Then, the distance between the upper electrode 104 and the lower electrode 101 changes, and therefore ultrasonic waves can be detected as change of the electrostatic capacitance.

As it is clear from the aforementioned principle of the operation, since CMUT transmits and receives ultrasonic waves by using vibration of the membrane induced by the electrostatic force resulting from application of voltage between the electrodes and capacitance change between the electrodes induced by the vibration, stability of voltage difference between the electrodes is important for stable operation and improvement in reliability of the device.

According to the aforementioned principle of operation, by applying a DC voltage between the upper electrode 104 and the lower electrode 101, an electrostatic force is generated between the two electrodes, and the membrane is deformed, and stabilized at a deformation amount at which the spring restoring forth induced by the deformation and the electrostatic force are balanced.

CMUT is usually driven at such a DC voltage that the electrostatic force between the electrodes and the spring restoring forth are balanced. However, if a DC voltage larger than such a voltage that deformation amount of the membrane reaches about ⅓ of the distance between the electrodes, called collapse voltage, is applied, the electrostatic force between the electrodes becomes larger than the spring restoring force of the membrane, thus the membrane cannot be stabilized at a fixed position, but a lower surface 106 of the membrane contacts with a lower surface 107 of the hollow part. If they contact, there is produced a structure that the insulating film 103 is held between the upper electrode and the lower electrode, and electrical charge is injected into the film from the two electrodes to generate fixed electrical charge in the film. Even if a DC voltage is applied again between the two electrodes, the electric field between the electrodes is shielded by the fixed electrical charge in the insulating film, and the voltage used for optimal operation of CMUT is changed. Therefore, the CMUTs disclosed in Patent documents 1, 2 and 3 are usually used with a voltage significantly lower than the collapse voltage in order to prevent the lower surface of the membrane from contacting with the lower surface of the hollow part.

However, in order to improve the sensitivity for transmission and reception, it is necessary to make the distance between the electrodes as short as possible during use of CMUT, and therefore it is important to apply a voltage as close to the collapse voltage as possible between the electrodes.

Moreover, in order to improve transmitting sound pressure of the ultrasonic waves, it is desirable to maximize the vibration amplitude of the membrane 105. However, in order to prevent the lower surface 106 of the membrane from contacting with the lower surface 107 of the hollow part and not to inject electrical charge into the insulating film during the vibration, the AC voltage to be superimposed on the DC voltage must also be a voltage significantly lower than the voltage at which the lower surface of the membrane contacts with the lower electrode or the insulating film under the hollow part.

Patent document 4 mentioned above discloses a structure that a projection of the insulating film protruding into the hollow part of CMUT is formed so that the projection serves as a support pillar, and thus the lower surface of the membrane except for the lower surface of the projection does not contact with the lower surface of the hollow part, even if a DC voltage or an AC voltage higher than the collapse voltage is applied. However, since it has a structure that the projection is positioned between the upper and lower electrodes, accumulation of electrical charge in the insulating film of the projection cannot be avoided.

In contrast, the CMUT of Patent document 5 has a structure that the projection of the insulating film protruding into the hollow part is not put between the upper and lower electrodes, and therefore accumulation of electrical charge in the insulating film of the projection can be avoided even when the lower surface of the projection contacts with the lower surface of the hollow part. However, if a large number of projections are disposed, the area of the overlapping part of the upper and lower electrodes correspondingly becomes small, which results in increase in driving voltage of CMUT and decrease in reception sensitivity, as is also clear from the aforementioned principle of the operation of CMUT. This situation is schematically shown in FIG. 2. FIG. 2, (a) is a schematic view of disposition pattern of projections of the insulating film protruding into the hollow part 102 seen from above. The hollow part has a rectangular shape as seen from above, and there are shown a projection 108 of the insulating film disposed at the center of the membrane locating above the hollow part, and representatively shown the n-th projections 109 of the insulating film, (n+2)th projections 110 of the insulating film, and the (n+4)th projections 111 of the insulating film among the projections disposed on both sides of the projection 108. Since the hollow part 102 has a rectangular shape, the membrane is symmetrically deformed by the voltage with respect to the projection 108 at the center of the membrane, and when the projections are disposed one after another, the number of the projections is increased by 2 at a time. If the number of the projections is increased from n to n+2, n+4, . . . , the voltage at which the lower surface of the membrane except for the lower surfaces of the projections contacts with the lower surface of the hollow part increases, and the area of the overlapping parts of the upper and lower electrodes decreases. This relation is schematically shown in FIG. 2, (b). As seen from FIG. 2, (b), in which X represents the driving voltage (volt) for CMUT for obtaining transmission and reception sensitivity for ultrasonic waves and transmitting sound pressure required for ultrasonic diagnosis, if the number of the projections is n, when the membrane vibrates, the lower surface of the membrane except for the lower surfaces of the projections contacts with the lower surface of the hollow part, and accumulation of electrical charge in the insulating film cannot be obviated. However, if the projections are increased without any restriction, the area of the overlapping parts of the upper and lower electrodes decreases, and receiving sensitivity becomes lower. In such a case, if n+2 of the projections are disposed, although the lower surfaces of n+2 of the projections contact with the lower surface of the hollow part at the driving voltage, they serve as support pillars, therefore the lower surface of the membrane except for the lower surfaces of the projections does not contact with the lower surface of the hollow part, thus accumulation of electrical charge in the insulating film can be suppressed, and decrease of the area of the overlapping parts of the upper and lower electrodes can also be suppressed.

Based on the above, an object of the present invention is, for disposing projections of insulating film protruding into a hollow part in CMUT, to provide a method for determining disposing positions and number of the projections, an ultrasonic transducer having projections of insulating film formed according to the disposition method, and an ultrasonic diagnostic apparatus using it.

The aforementioned object and the other objects as well as the novel characteristics of the present invention will become apparent from the descriptions of this specification and the appended drawings.

Means for Achieving the Object

Brief explanations of the outlines of the representative embodiments of the present invention disclosed in this application are as follows.

The ultrasonic transducer of the present invention is an ultrasonic transducer comprising a first electrode, a lower insulating film formed on the first electrode, an upper insulating film provided so as to form a hollow part above the lower insulating film, and a second electrode formed on the upper insulating film, wherein the lower insulating film or the upper insulating film has projections formed on the side of the hollow part, and the first electrode or the second electrode has openings formed at positions corresponding to the positions at which the projections are formed.

The ultrasonic transducer of the present invention may be characterized in that a first projection is formed on the upper insulating film or the lower insulating film at a position corresponding to the center of a membrane consisting of at least the upper insulating film and the second electrode.

The ultrasonic transducer of the present invention may be characterized in that a second projection is formed between the first projection and an edge of the hollow part, and, provided that the first projection is contacted with the upper insulating film or the lower insulating film and a part of the membrane on a straight line connecting the first projection and an edge of the hollow part is contacted with the lower insulating film by driving voltage applied to the first electrode and the second electrode, the second projection is formed at the contacting part of the membrane.

The ultrasonic transducer of the present invention may be characterized in that a third projection is formed between the second projection and the edge of the hollow part, and provided that a part of the membrane on a straight line connecting the second projection and the edge of the hollow part is contacted with the lower insulating film by driving voltage applied to the first electrode and the second electrode, the third projection is formed on the contacting part of the membrane.

The ultrasonic transducer of the present invention may be characterized in that a third projection is formed between the second projection and the edge of the hollow part, and provided that a part of the membrane on the straight line connecting the second projection and the edge of the hollow part is contacted with the lower insulating film by driving voltage applied to the first electrode and the second electrode, the third projection is formed at a position shifted to the first projection side from the contacting part of the membrane.

The ultrasonic transducer of the present invention may be characterized in that, provided that the membrane is contacted with the lower insulating film between the first projection and the second projection by driving voltage applied to the first electrode and the second electrode, a third projection is further formed at the middle point between the first projection and the second projection.

The ultrasonic transducer array of the present invention comprises the ultrasonic transducers disposed in an array, wherein the ultrasonic transducers have different disposition patterns of projections.

Further, the ultrasonic diagnostic apparatus of the present invention comprises an ultrasonic probe for transmitting and receiving ultrasonic waves to or from a subject, an image processing part for constituting an ultrasonogram on the basis of received ultrasonic signals outputted from the ultrasonic probe, and a display part for displaying the ultrasonogram, wherein the ultrasonic probe is an ultrasonic transducer comprising a first electrode, a lower insulating film formed on the first electrode, an upper insulating film provided so as to form a hollow part above the lower insulating film, and a second electrode formed on the upper insulating film, wherein the lower insulating film or the upper insulating film has projections formed on the side of the hollow part, and the first electrode or the second electrode has openings formed at positions corresponding to the positions at which the projections are formed.

The ultrasonic diagnostic apparatus of the present invention may be characterized by using an ultrasonic transducer in which a first projection is formed on the upper insulating film or the lower insulating film at a position corresponding to the center of the membrane consisting of at least the upper insulating film and the second electrode.

The ultrasonic diagnostic apparatus of the present invention may be characterized by using the ultrasonic transducer, wherein, provided that the first projection is contacted with the upper insulating film or the lower insulating film and a part of the membrane on a straight line connecting the first projection and an edge of the hollow part is contacted with the lower insulating film by driving voltage applied to the first electrode and the second electrode, a second projection is formed on the contacting part of the membrane.

The ultrasonic diagnostic apparatus of the present invention may be characterized by using the ultrasonic transducer, wherein, provided that a part of the membrane on a straight line connecting the second projection and the edge of the hollow part is contacted with the lower insulating film by driving voltage applied to the first electrode and the second electrode, a third projection is formed on the contacting part of the membrane.

The ultrasonic diagnostic apparatus of the present invention may be characterized by using the ultrasonic transducer, wherein, provided that the membrane is contacted with the lower insulating film at a position on the straight line connecting the second projection and the edge of the hollow part by driving voltage applied to the first electrode and the second electrode, a third projection is formed at a position shifted to the first projection side from the contacting part of the membrane.

The ultrasonic diagnostic apparatus of the present invention may be characterized by using the ultrasonic transducer, wherein, provided that the membrane is contacted with the lower insulating film between the first projection and the second projection by driving voltage applied to the first electrode and the second electrode, the third projection is formed at the middle point between the first projection and the second projection.

The ultrasonic diagnostic apparatus of the present invention may be characterized by using an ultrasonic transducer array comprising the ultrasonic transducers disposed in an array, wherein the ultrasonic transducers have different disposition patterns of projections.

Effect of the Invention

Effects obtainable by the representative embodiments of the present invention among those disclosed in this application are briefly explained as follows.

According to the present invention, when a CMUT is contemplated, in which projections of an insulating film protruding into a hollow part are disposed in order to suppress injection of electrical charge into the insulating film due to contact thereof between a lower surface of the hollow part and a lower surface of the membrane, there can be provided a ultrasonic transducer (CMUT) having a projection disposition structure suitable for suppressing increase in driving voltage of the CMUT and decrease in receiving sensitivity, and an ultrasonic diagnostic apparatus using the same.

BRIEF DESCRIPTION OF THE DRAWINGS

FIG. 10 shows sections along the line A-A' drawn in FIG. 7, in which the projections of the insulating film have different lengths: (a) shows a state that voltage for driving the CMUT is not applied, and (b) shows a state that voltage for driving the CMUT is applied, and the projections of the insulating film contact with the lower surface of the hollow part.

MODES FOR CARRYING OUT THE INVENTION

Hereafter, embodiments of the present invention will be explained in detail with reference to the drawings. In all the drawings for explaining the embodiments, the same members are basically indicated with the same numerals, and repetitive explanations for them are omitted.

In the following explanations of the embodiments, explanations are made with several sections or for several embodiments for convenience, as required, but they are mutually related, and are in such a relation that one of them is modification, details, supplemental explanation or the like of a part or all of the other, unless especially indicated.

Moreover, in the following explanations of the embodiments, when a number of an element (including number, numerical value, quantity, range etc.) or the like is mentioned, the number is not limited to that specific number, and may be larger or smaller than the mentioned number, except for the case where it is explicitly indicated that the number should be the specifically mentioned number, or it is theoretically clear that the number should be limited to the specifically mentioned number.

Furthermore, in the embodiments mentioned below, it is of course that the constituent elements thereof (including steps as elements etc.) are not necessarily indispensable, except for the case where it is explicitly indicated that a specific element is indispensable, or it is theoretically clear that a specific element is indispensable.

Similarly, in the following explanations of the embodiments, when shapes, positional relationship etc. of the constituent elements are mentioned, they include substantially similar or analogous shapes and so forth, except for the case where it is explicitly indicated, or it is theoretically clear that the above is not true. This shall also apply to the numerical values and ranges mentioned above.

In addition, even in a plane view, hatching may be used for ease of understanding.

<Ultrasonic Transducer>

In the following embodiment, the object of producing an ultrasonic transducer comprising suitably disposed projections of an insulating film protruding into a hollow part is achieved by determining disposing position of a projection and necessity of disposition of a projection on the basis of determining which one of driving voltage for the ultrasonic transducer applied by an ultrasonic diagnostic apparatus and voltage at which the lower surface of the membrane contacts with the lower surface of the hollow part is larger than the other.

Embodiment 1

Figure 1:
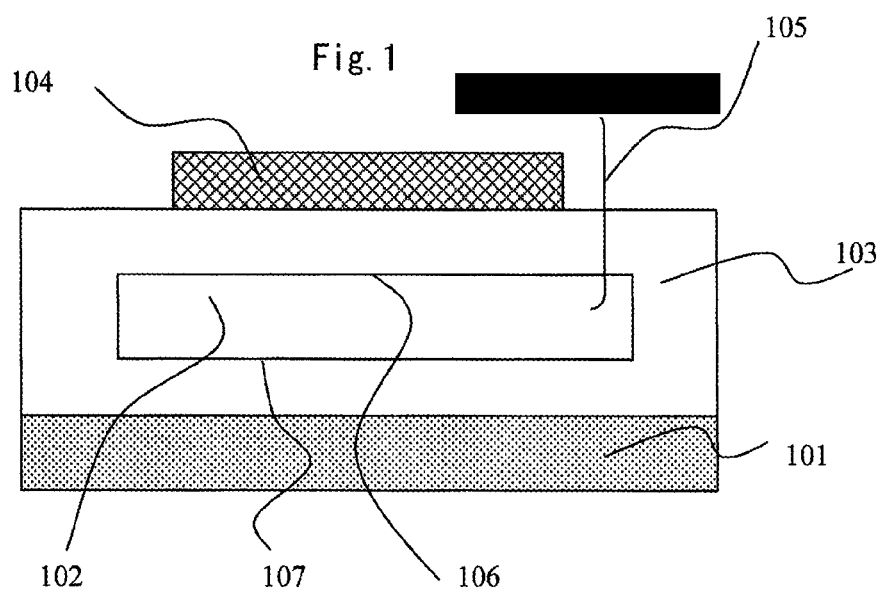
FIG. 1 is a sectional view of an ultrasonic transducer examined by the inventors of the present invention.
Figure 2:
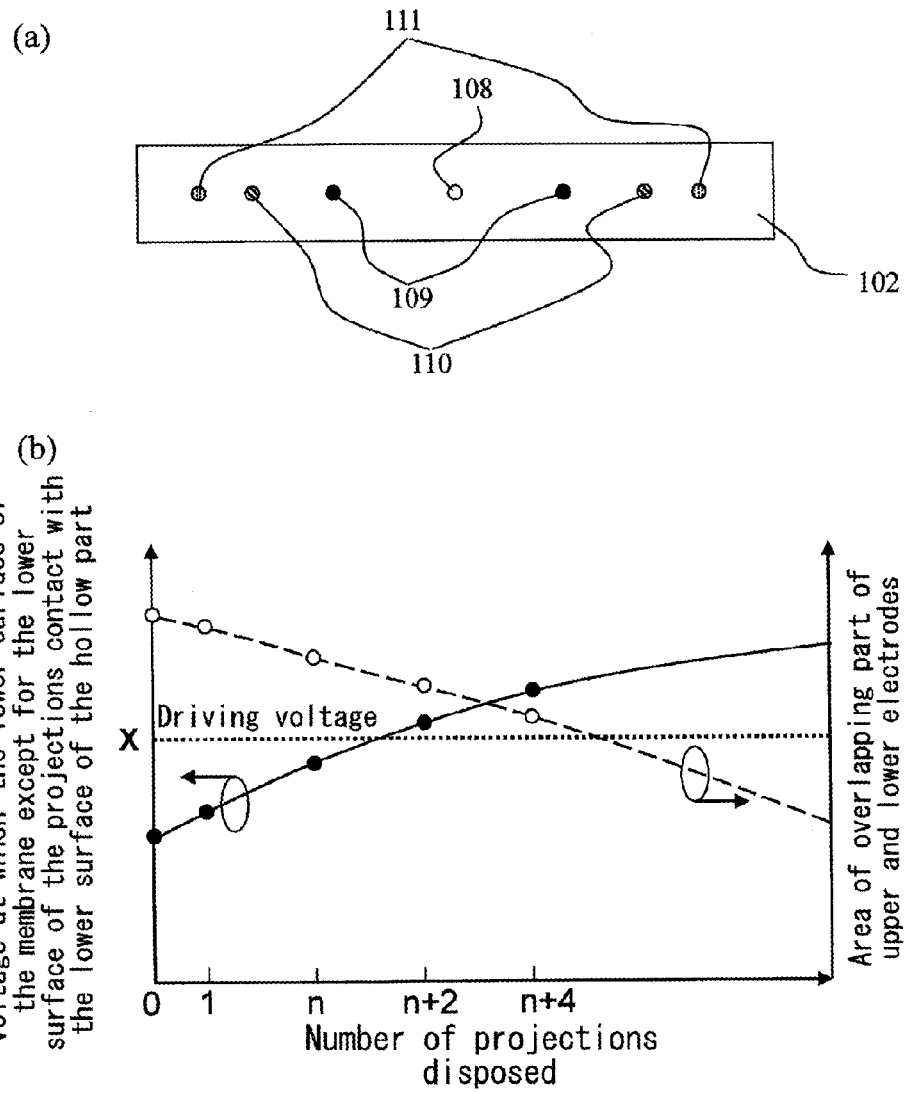
FIG. 2, (a) is a schematic view of a disposition pattern of projections for disposing projections in a hollow part, which is seen from above, and (b) is a graph showing the relation between number of disposed projections and overlapping area of upper and lower electrodes, and the relation between number of disposed projections and voltage (contact voltage) at which the lower surface of the membrane except for projections contacts with the lower surface of the hollow part.
Figure 3:
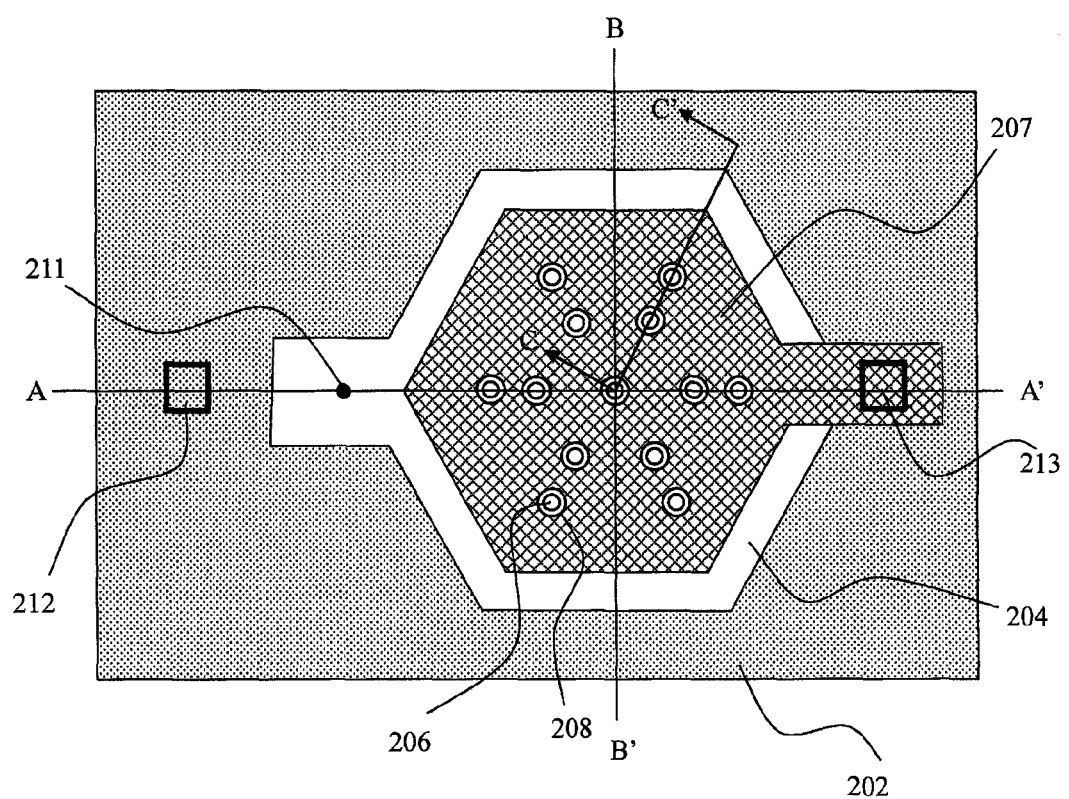
FIG. 3 is a top view of the ultrasonic transducer according to the embodiment 1 of the present invention, in which the hollow part has a hexagonal shape as seen from above.
Figure 4:
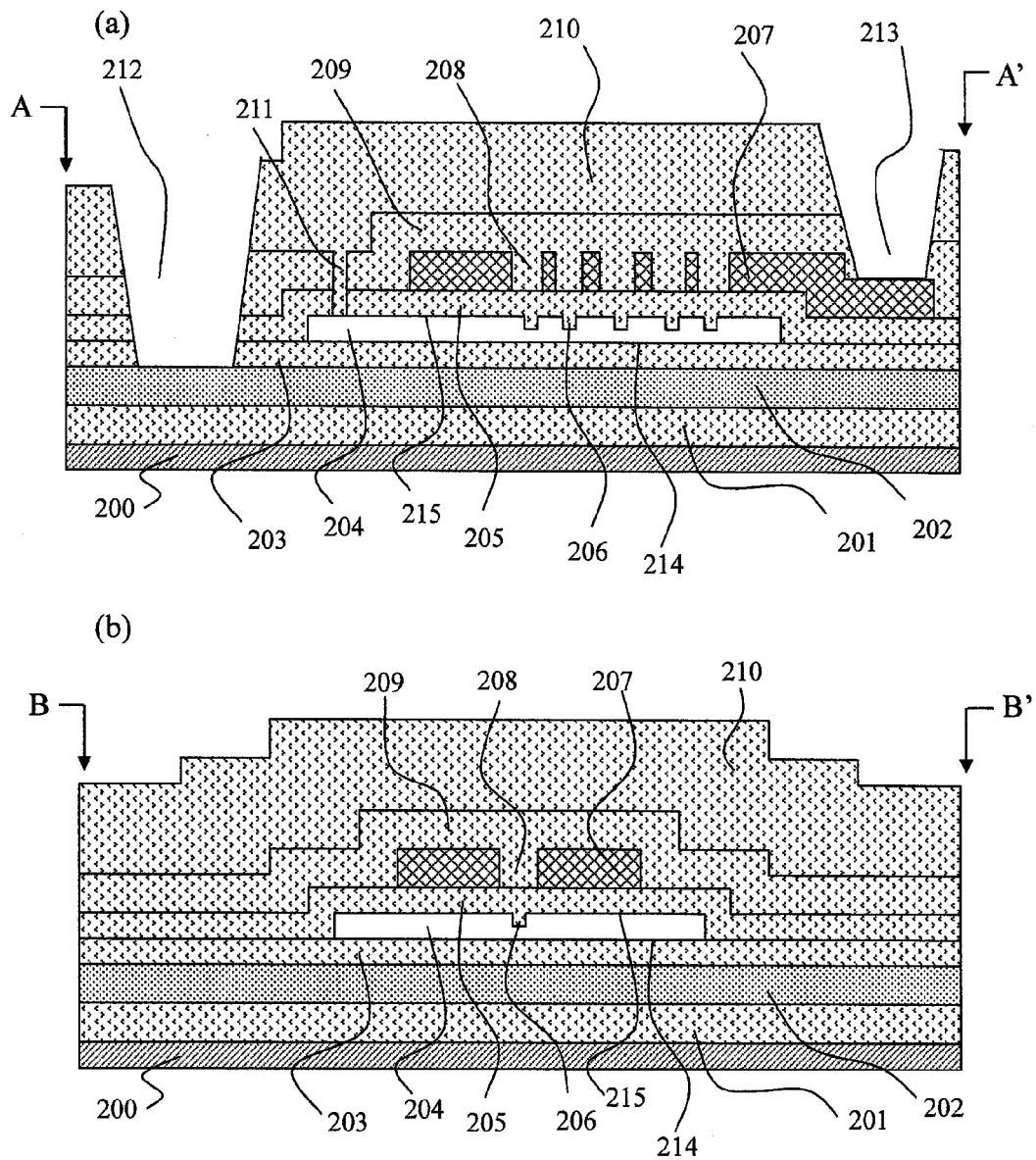
FIG. 4, (a) is a sectional view along the line A-A' drawn in FIG. 3, and (b) is a sectional view along the line B-B' drawn in FIG. 3.

A structure of an ultrasonic transducer (CMUT) according to the embodiment 1 of the present invention will be explained with reference to FIGS. 3 and 4. FIG. 3 is a top view of the ultrasonic transducer (CMUT) of this embodiment 1. FIG. 4, (a) is a sectional view along the line A-A' drawn in FIG. 3, and FIG. 4, (b) is a sectional view along the line B-B' drawn in FIG. 3.

FIG. 3 shows one CMUT cell. The CMUT cell comprises a lower electrode 202, a hollow part 204 formed above the lower electrode 202, projections 206 of an insulating film consisting of a silicon oxide film, formed so as to protrude into the hollow part 204, an upper electrode 207 formed above the hollow part 204, and so forth. A wet etching hole 211 for forming the hollow part is communicated with the space serving as the hollow part 204. An opening 212 is provided so as to reach the lower electrode 202, and an opening 213 is provided so as to reach the upper electrode 207. Between the upper electrode 207 and the hollow part 204, the insulating film 205 consisting of a silicon oxide film is formed so as to cover the hollow part 204 and the lower electrode 202, and between the lower electrode 202 and the hollow part 204, the insulating film 203 consisting of a silicon oxide film is formed so as to cover the lower electrode. However, these insulating films are not shown in FIG. 3, in order to show the hollow part 204 and the lower electrode 202. An opening 208 is provided in the upper electrode 207 so that the upper electrode 207 does not overlap with the projection 206 as seen from above. By providing the opening in the upper electrode 207, accumulation of electrical charge in the projection, which consists of the insulating film, can be prevented.

As shown in FIGS. 4, (a) and (b), the lower electrode 202 of the CMUT is formed on the insulating film 201 consisting of the silicon oxide film and formed on a semiconductor substrate 200. Above the lower electrode 202, the hollow part 204 is formed via the insulating film 203 consisting of a silicon oxide film. The insulating film 205 consisting of a silicon oxide film is formed so as to surround the hollow part 204, and the upper electrode 207 is formed on the insulating film 205. On the lower surface of the insulating film 205, the projections 206 consisting of a silicon oxide film are formed so as to protrude into the hollow part 204, and the openings 208 are formed in the upper electrode 207 above the projection 206. An insulating film 209 and an insulating film 210 consisting of silicon nitride films are formed on the upper electrode 207. Further, the wet etching hole 211 is formed in the insulating film 205 and the insulating film 209 so as to penetrate these films. This wet etching hole 211 is formed to produce the hollow part 204, and it is filled with the insulating film 210 after the formation of the hollow part 204.

In the CMUT shown in FIGS. 3 and 4, as seen from above, there are disposed one projection at the center of the membrane, and two projections on each diagonal line of the hexagon starting from the center of the membrane and going toward the edge of the hollow part, and this disposition pattern of the projections is determined by the method explained with reference to FIGS. 5 and 6.

Figure 5:
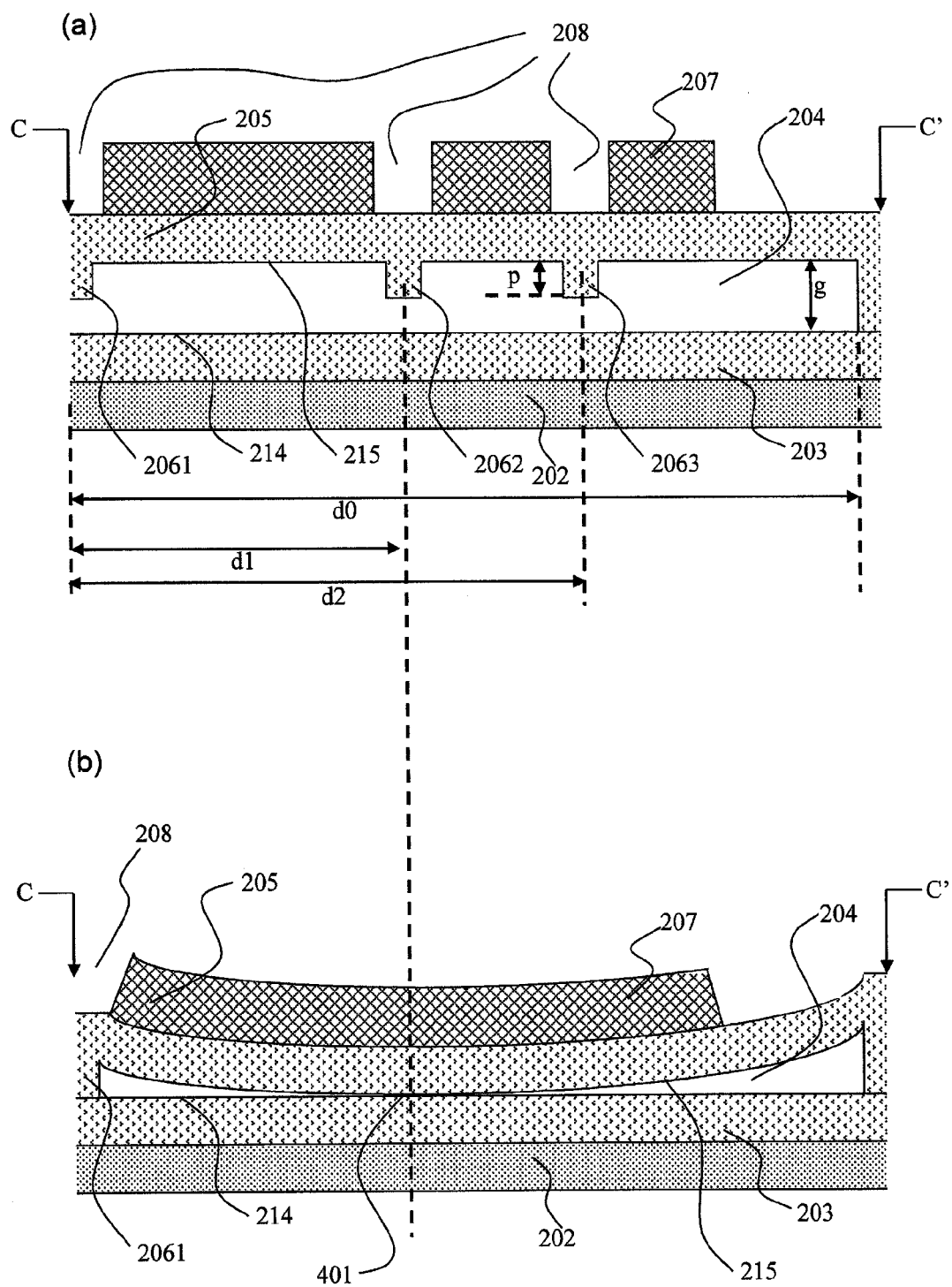
FIG. 5, (a) shows a sectional along the line C-C' drawn in FIG. 3, showing a state that voltage for driving the CMUT is not applied, and (b) shows a section along the line C-C' drawn in FIG. 3, showing a CMUT where the projections 2062 and 2063 are not disposed, but only the projection 2061 is disposed, and which is driven by an ultrasonic diagnostic apparatus, so that the projection 2061 contacts with the lower surface 214 of the hollow part, and the lower surface 215 of the membrane contacts with the lower surface 214 of the hollow part.

FIG. 5, (a) is a sectional view along the line C-C' drawn in FIG. 3, and shows a state that voltage for driving the CMUT is not applied by an ultrasonic diagnosis apparatus, and the lower electrode 202, the lower insulating film 203, the hollow part 204, the upper insulating film 205, the projections 206, and the upper electrode 207 are selectively shown. The projections 206 consisting of the insulating film are numbered 2061, 2062 and 2063, respectively, from the center of the membrane (on the side of C of the section along C-C') to the edge of the hollow part (on the side of C' of the section along C-C') as seen from above.

FIG. 5, (b) shows a state that the projections 2062 and 2063 shown in FIG. 5, (a) are not disposed, but only the projection 2061 is disposed, and when the CMUT is driven by an ultrasonic diagnostic apparatus, the lower surface of the projection 2061 contacts with the lower surface 214 of the hollow part, and the lower surface 215 of the membrane except for the lower surface of the projection contacts with the lower surface 214 of the hollow part.

The procedure for determining the disposition pattern of the projections shown in FIG. 5, (a) is as follows.

In this procedure, the driving voltage V0 for CMUT applied by an ultrasonic diagnostic apparatus is compared with the voltage V at which the lower surface of the membrane contacts with the lower surface of the hollow part. The voltage V changes with change of size of the intended membrane, and can be determined by performing simulation using the finite element method (FEM) in the step of designing the CMUT. Alternatively, it may be determined by performing applied voltage-capacitance measurement for a trial product device. The former method is preferred, since the voltage V can be obtained, and the disposition pattern of the projections can be determined in the step of designing.

First, when the driving voltage V0 for CMUT applied by an ultrasonic diagnostic apparatus is equal to or larger than the voltage V1 at which the lower surface 215 of the membrane contacts with the lower surface 214 of the hollow part at the center of the membrane, and thus the lower surface 215 is contacted with the lower surface 214 of the hollow part by applying the driving voltage, the projection 2061 is disposed at the center of the membrane.

Further, as for the membrane supported by the projection 2061 at the center of the membrane and the edge of the hollow part shown in FIG. 5, (b), when the driving voltage V0 for CMUT applied by an ultrasonic diagnostic apparatus is equal to or larger than the voltage V2 at which the lower surface of the membrane contacts with the lower surface of the hollow part, and thus the lower surface 215 of the membrane is contacted with the lower surface of the hollow part by applying the driving voltage V0, then the projection 2062 is disposed at the contacting part 401. The disposing position of the projection, that is, the position x at which the lower surface of the membrane extending from the projection 2061 at the center of the membrane contacts with the lower surface of the hollow part, is determined according to which one of spring repulsive force of the membrane and electrostatic attractive force between the electrodes is larger than the other at the position x. The spring repulsive force is determined by spring constant of the membrane and amount of displacement of the membrane at the contacting position, the electrostatic attractive force is determined by electrode area and distance between the electrodes at the position x, and they can be obtained by performing a simulation.

Figure 6:
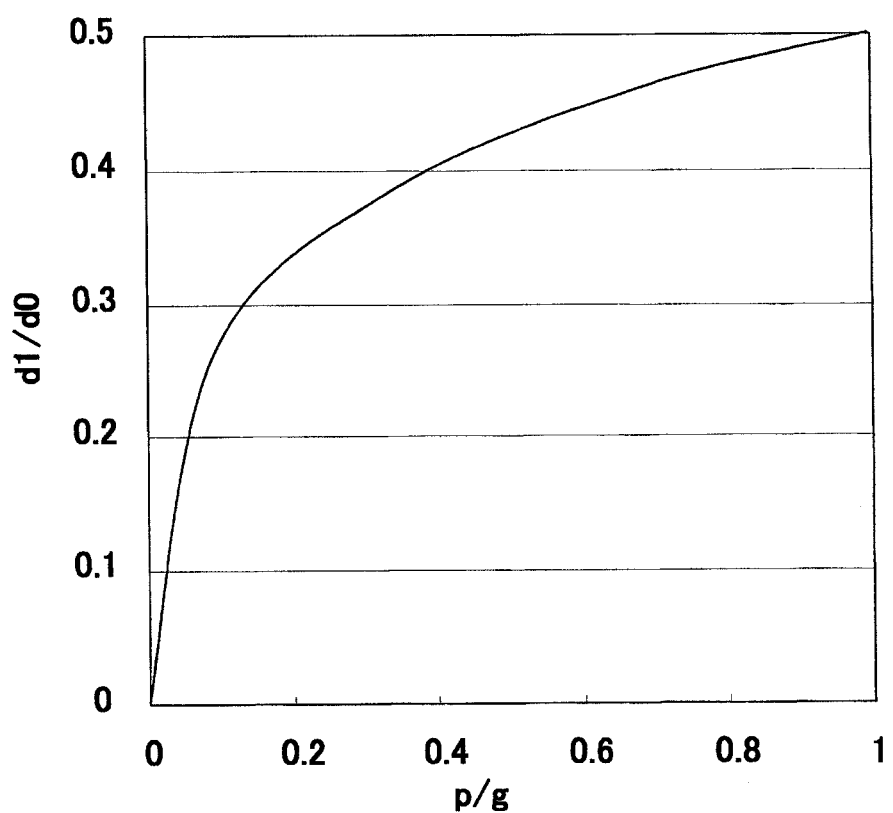
FIG. 6 is a graph showing the relation of the distance d1 indicating disposing position of a projection, length p of the projection, thickness g of the hollow part, and distance d0 between the center of the membrane and the edge of the hollow part.

A graph showing the relation of the distance from the projection 2061 at the center to the contacting position 401, that is, the distance d1 indicating the position at which the second projection 2062 is to be disposed, thickness g of the hollow part, the distance d0 between the center of the membrane and the edge of the hollow part, and length p of the projection obtained by a simulation is shown in FIG. 6. The horizontal axis of the graph shown in FIG. 6 indicates [length p of the projection]/[thickness g of the hollow part], and the vertical axis indicates [distance d1 indicating the projection disposing position]/[distance d0 from the center to the edge]. The distance d1 indicating the disposing position of the second projection can be determined on the basis of this relation.

In this embodiment 1, provided that the length p of the projection is 80 nm, the thickness g of the hollow part is 200 nm, the distance d0 from the center of the membrane to the edge of the hollow part is 100 μm, for example, d1 is determined to be 40 μm on the basis of the relation shown in FIG. 6, and the projection 2062 is disposed at a distance of 40 μm from the projection 2061.

The disposing position of the projection 2063 can also be determined in a similar manner. That is, as for the membrane supported by the projection 2062 and the edge of the hollow part, provided that the lower surface 215 of the membrane is contacted with the lower surface of the hollow part by the driving voltage for the CMUT applied by an ultrasonic diagnostic apparatus, the projection 2063 is disposed at the contacting part. Also in this case, the disposing position can be determined on the basis of the relation shown in FIG. 6. The distance d0–d1 between the projection 2062 and the edge of the hollow part corresponds to d0 used for determining the distance d1 for disposing the projection 2062, and d2–d1 corresponds to d1. Specifically, the length p of the projection and the thickness g of the hollow part are the same, that is, they are 80 nm and 200 nm, respectively, d0 is 100 μm, and d1 is 40 μm. Therefore, d0–d1 is 60 μm, and d2–d1 is 24 μm. Accordingly, d2 is 64 μm, and the projection 2063 is disposed at a distance of 64 μm from the projection 2061 at the center of the membrane.

When the projections 2061, 2062 and 2063 are contacted with the lower surface of the hollow part by the driving voltage for CMUT applied by an ultrasonic diagnostic apparatus, and the lower surface 215 of the membrane at a part between the projections or projection and edge of the hollow part is not contacted with the lower surface 214 of the hollow part, it is not necessary to further dispose projections. However, when the projections 2061, 2062 and 2063 are contacted with the lower surface of the hollow part by the driving voltage for CMUT applied by an ultrasonic diagnostic apparatus, and the lower surface 215 of the membrane at a part between the projections or projection and edge of the hollow part is further contacted with the lower surface 214 of the hollow part, a further projection can be disposed in a similar manner.

Although the above explanation was made with reference to FIG. 5 showing sections along the line C-C' drawn in FIG. 3, disposing positions of the projections for the other sections can also be determined in a similar manner. Further, since the hollow part of the CMUT shown in FIG. 3 has a hexagonal shape as seen from above, it has rotational symmetry of 60 degrees with respect to the center, and there may be disposed one projection at the center of the membrane, and two projections on each diagonal line of the hexagon starting from the center of the membrane and going toward the edge of the hollow part.

As described above, this embodiment 1 is characterized in that necessity of disposition of a projection of an insulating film is determined on the basis of comparison of the driving voltage for CMUT applied by an ultrasonic diagnostic apparatus and the voltage at which the lower surface of the membrane contacts with the lower surface of the hollow part, and the disposing positions of the projections are determined on the basis of the relation shown in FIG. 6.

By using this procedure, the necessary minimum number of the projections to be disposed can be determined. Therefore, even when the electrode is disposed so that it does not overlap with the projections of the insulating film as seen from above (in this embodiment, openings are provided in the upper electrode so that the electrode should not overlap with the projections of the insulating film), undue increase of the driving voltage for CMUT and decrease in receiving sensitivity resulting from unduly small overlapping area of the upper and lower electrodes can be suppressed.

When the disposing positions of the projections are determined on the basis of the relation shown in FIG. 6, even if the projection do not exactly locate at the positions determined by using the curves shown FIG. 6, equivalent effect can be obtained if they are disposed at such positions that amount of displacement of the membrane at the position at which the lower surface of the membrane contacts with the lower surface of the hollow part changes by up to −10% compared with that observed at the position determined on the basis of the relation shown in FIG. 6. Specifically, the range of the distance providing the change of the amount of membrane displacement of up to −10% is 0.8d1 to 1.2d1, wherein d1 is the distance to the contacting position.

Further, when a projection is disposed at a position at which the membrane supported by a projection and the edge of the hollow part contacts with the lower surface of the hollow part, like the projection 2062 or 2063 shown in FIG. 5, such a projection is preferably disposed at a position closer to the membrane center than the position determined on the basis of the relation shown in FIG. 6 for suppressing contact of the lower surface of the membrane with the lower surface of the hollow part.

Figure 7:
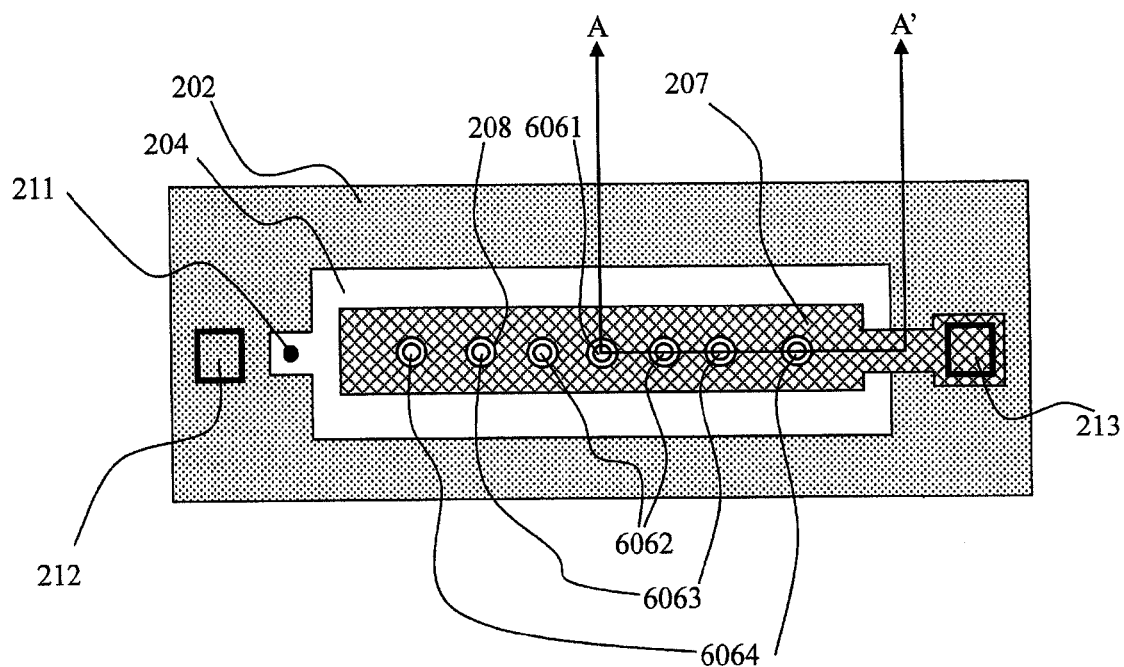
FIG. 7 is a top view of the ultrasonic transducer according to the embodiment 1 of the present invention, in which the hollow part has a rectangular shape as seen from above.

Hereafter, another example of the embodiment 1 will be explained with reference to FIGS. 7 and 8. FIG. 7 is a top view of a CMUT cell, and FIG. 8 shows a section along the line A-A' drawn in FIG. 7.

As shown in FIG. 7, the CMUT cell of this example has the hollow part having a rectangular shape as seen from above, and constituted by the lower electrode 202, the hollow part 204 formed above the lower electrode 202, the projections 6061, 6062, 6063 and 6064 of the insulating film consisting of a silicon oxide film, formed so as to protrude into the hollow part 204, the upper electrode 207 formed above the hollow part 204, and so forth. The wet etching hole 211 for forming the hollow part is communicated with the space serving as the hollow part 204. The opening 212 is provided so as to reach the lower electrode 202, and the opening 213 is provided so as to reach the upper electrode 207. Between the upper electrode 207 and the hollow part 204, the insulating film 205 consisting of a silicon oxide film is formed so as to cover the hollow part 204 and the lower electrode 202, and between the lower electrode and the hollow part, the insulating film 203 consisting of a silicon oxide film is formed so as to cover the lower electrode. However, these insulating films are not shown in the drawing, in order to show the hollow part 204 and the lower electrode 202. The openings 208 are provided in the upper electrode 207 so that the upper electrode 207 does not overlap with the projections 6061, 6062, 6063 and 6064 as seen from above.

Figure 8:
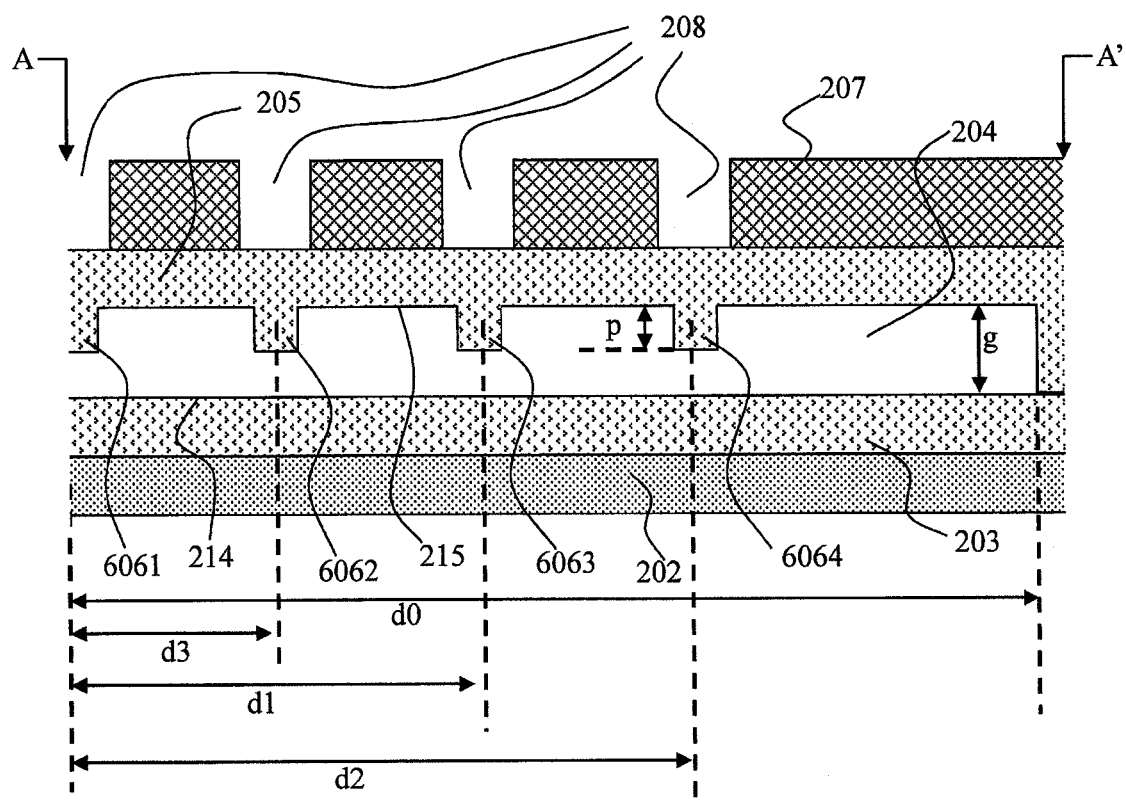
FIG. 8 shows a section along the line A-A' drawn in FIG. 7, showing a state that voltage for driving the CMUT is not applied.

FIG. 8 show a section along the line A-A' drawn in FIG. 7, and representatively shows the lower electrode 202, the lower insulating film 203, the hollow part 204, the upper insulating film 205, projections of the insulating film, and the upper electrode 207. The other configurations are the same as those shown in FIG. 4. The projections of the insulating film are numbered 6061, 6062, 6063 and 6064 from the projection at the center of the membrane (on the side of A of the section along A-A') toward the edge of the hollow part (on the side of A' of the section along A-A') as seen from above.

The procedure for determining the disposing positions of the projections 6061, 6062, 6063 and 6064 is the same as the procedure explained with reference to FIGS. 5 and 6. First, when the lower surface 215 of the membrane at the center of the membrane is contacted with the lower surface 214 of the hollow part by the driving voltage for CMUT applied by an ultrasonic diagnostic apparatus, the projection 6061 is disposed at the center of the membrane.

Further, as for the membrane in which the projection 6061 at the center of the membrane contacts with the lower surface 214 of the hollow part 204, and thus which is supported by the projection 6061 and the edge of the hollow part, when the lower surface 215 of the membrane except for the lower surface of the projection is contacted with the lower surface 214 of the hollow part by the driving voltage for CMUT applied by an ultrasonic diagnostic apparatus, the projection 6063 is disposed at the contacting part. In this case, the distance from the projection 6061 at the center of the membrane to the contacting position, that is, the distance d1 indicating the position at which the projection 6063 is to be disposed, the thickness g of the hollow part, the distance d0 between the center of the membrane and the edge of the hollow part, and the length p of the projection are in the relation shown in FIG. 6 as in the case explained above, and d1 can be determined on the basis of the relation.

Then, the disposing position of the projection 6064 can also be determined in the same manner. That is, as for the membrane in which the projection 6063 contacts with the lower surface 214 of the hollow part 204, and thus which is supported by the projection 6063 and the edge of the hollow part, when the lower surface 215 of the membrane is contacted with the lower surface 214 of the hollow part by the driving voltage for CMUT applied by an ultrasonic diagnostic apparatus, the projection 6064 is disposed at the contacting part. Also in this case, the disposing position can be determined on the basis of the relation shown in FIG. 6.

Further, the disposing position of the projection 6062 can also be determined in the same manner. That is, as for the membrane in which the projections 6061 and 6063 contact with the lower surface of the hollow part, and thus which is supported by the projections 6061 and 6063, when the lower surface 215 of the membrane is contacted with the lower surface 214 of the hollow part by the driving voltage for CMUT applied by an ultrasonic diagnostic apparatus, the projection 6062 is disposed at the contacting part. In this case, since the projections 6061 and 6063 have the same length, that is, the length p of the projection and the thickness g of hollow part are the same, the lower surface of the membrane contacts with the lower surface of the hollow part at the middle point between the projections 6061 and 6063 according to the relation of FIG. 6. Therefore, the projection 6062 can be disposed at the middle point between the projections 6061 and 6063.

Figure 9:
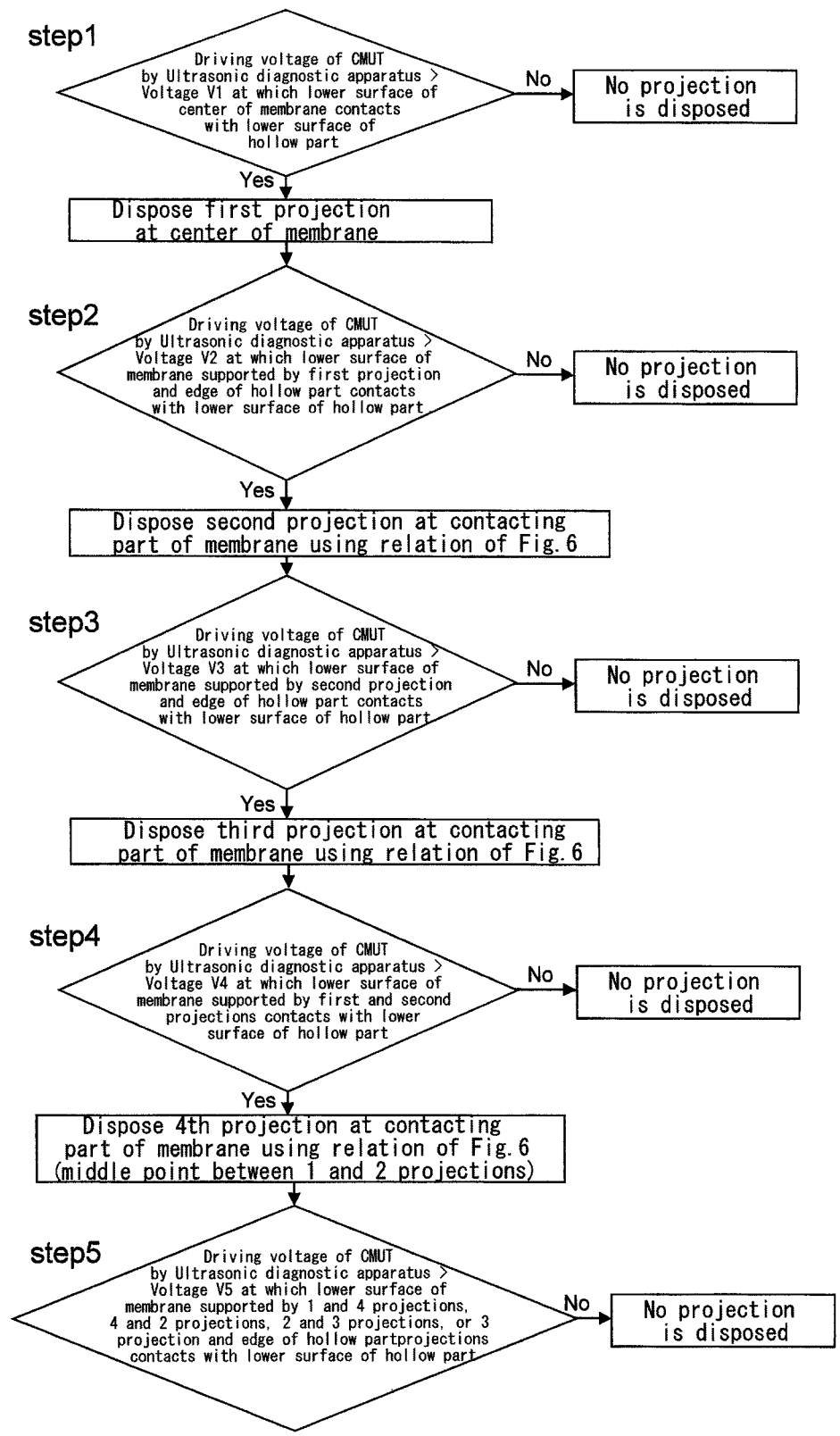
FIG. 9 is a flowchart for determining whether it is necessary to dispose a projection for the case that projections of an insulating film are disposed in the embodiment 1 of the present invention.

FIG. 9 is a flowchart of the aforementioned procedure for determining necessity of disposition of the projection and disposing position thereof. In each step, the driving voltage V0 for CMUT applied by an ultrasonic diagnostic apparatus and the voltage Vi (i=1, 2, 3 . . . k+1, and k is a number of projections to be finally disposed, including the center projection to the end projection) at which the lower surface of the membrane except for the lower surfaces of the projections contacts with the lower surface of the hollow part are compared to determine whether the lower surface of the membrane contacts with the lower surface of the hollow part, and when it is determined that the lower surface of the membrane contacts with the lower surface of the hollow part, a projection is disposed at the contacting point. When a projection is disposed, disposing position of the projection is determined on the basis of the relation shown in FIG. 6, and projections are further disposed in the same flow of the process, until the lower surface of the membrane is no longer contacted with the lower surface of the hollow part by the driving voltage for CMUT.

In the example shown in FIGS. 7 to 9, the projections 6061 to 6064 are disposed. However, if the driving voltage for CMUT applied by an ultrasonic diagnostic apparatus may be low, it is not necessary to dispose those projections, that is, no projection may be disposed, only the projection 6061 may be disposed, or only the projections 6061 and 6063 may be disposed. Further, order of determinations of necessities of disposing the projections 6064 and 6062 is also determined according to which one of the voltages which make the lower surface of the membrane contact with the lower surface of the hollow part at the positions where the projections are disposed is larger than the other, and it is apparent that there may be a case where it is necessary to dispose the projection 6062, but it is not necessary to dispose the projection 6064.

Moreover, it is of course that, at the time of determining necessity of disposing a projection, it is necessary to take into consideration stability of the driving voltage and variation of the contact voltage of the membrane caused by manufacturing error occurring in the manufacture of CMUTs.

As described above, by comparing the driving voltage for CMUT applied by an ultrasonic diagnostic apparatus and the voltage at which the lower surface of the membrane contacts with the lower surface of the hollow part to determine necessity of disposing a projection of the insulating film, and determining disposing position of the projection on the basis of the relation shown in FIG. 6, the necessary minimum number of the projections can be disposed. Therefore, even when the electrode is disposed so that it does not overlap with the projections of the insulating film as seen from above, undue increase of the driving voltage for CMUT and decrease in receiving sensitivity resulting from unduly small overlapping area of the upper and lower electrodes can be suppressed.

Although the projections used in the embodiment 1 have such a structure that they protrude into the hollow part from the lower surface of the membrane, the same effect can be obtained with a structure that they protrude from the lower surface of the hollow part, and the projections can be disposed on the basis of the relation shown in FIG. 6 according to the procedure shown in FIG. 9.

Further, although the projections have the same length within the membrane in the embodiment 1, the amount of deformation of the membrane induced by the driving voltage for CMUT becomes largest at the center of the membrane and decreases as the position becomes closer to the edge of the hollow part, therefore, a short projection may be disposed at the center of the membrane seen from above, and a longer projection may be disposed as the position becomes closer to the edge of the hollow part as shown in FIG. 10. By using such a disposition pattern, a further larger amplitude of the vibration of the membrane can be used. Also in this case, necessity of disposition of a projection can be judged according to the procedure shown in FIG. 9, and the disposing position of the projection can be determined on the basis of the relation shown in FIG. 6.

In the examples explained for the embodiment 1, openings are provided in upper electrode as a structure for avoiding overlapping of the electrode and the projections as seen from above. The same shall apply to the case where openings are provided in the lower electrode at positions overlapping with projections. Also in such a case, necessity of disposition of a projection and disposing position of the projection can be judged and determined according to the same procedure, openings can be provided in the lower electrode provided under the projections, then the openings of the lower electrode can be filled with the insulating film, and then the hollow part, the membrane, and so forth can be formed.

Embodiment 2

In contrast to the embodiment 1 relating to disposition of projections in a single CMUT cell, the embodiment 2 relates to disposition of projections in a transducer comprising a plurality of CMUT cells disposed in an array.

Figure 11:
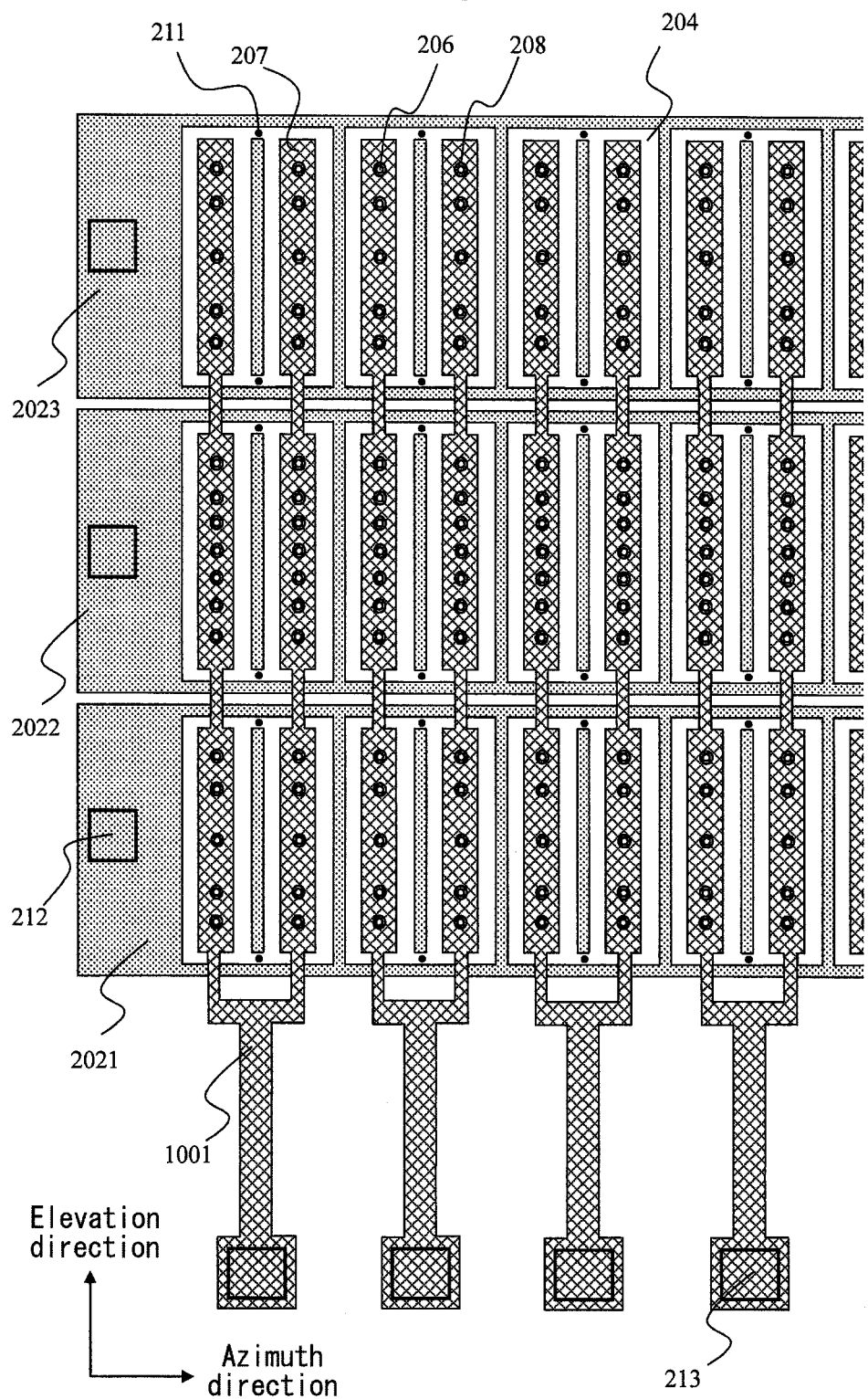
FIG. 11 is a top view of a chip on which the ultrasonic transducers are disposed in an array according to the embodiment 2 of the present invention.

FIG. 11 shows a part of chip consisting of rectangular CMUT cells disposed in an array. As the CMUT shown in FIG. 3, each CMUT comprises the lower electrode 2021, 2022 or 2023, the hollow part 204 formed above the lower electrode 2021, 2022 or 2023, the projections 206 of the insulating film consisting of a silicon oxide film formed so as to protrude into the hollow part 204, the upper electrode 207 formed above the hollow part 204, and so forth, and the wet etching hole 211 for forming the hollow part is communicated with the space serving as the hollow part 204. The opening 212 is provided so as to reach the lower electrode 202, and the opening 213 is provided so as to reach the upper electrode 207. Between the upper electrode 207 and the hollow part 204, the insulating film 205 consisting of a silicon oxide film is formed so as to cover the hollow part 204 and the lower electrode 2021, 2022 or 2023, and between the lower electrode 2021, 2022 or 2023 and the hollow part 204, the insulating film 203 consisting of a silicon oxide film is formed so as to cover the lower electrode 2021, 2022 or 2023. However, these insulating films are not shown in the drawing, in order to show the hollow part 204 and the lower electrode 2021, 2022 or 2023. The opening 208 is provided in the upper electrode 207 so that the upper electrode 207 does not overlap with the projection 206 as seen from above. The layer structure of each CMUT cell shown in FIG. 11 for the sectional direction is the same as that shown in FIG. 4.

In the array, the disposition directions of the upper electrodes and the lower electrodes are perpendicular to each other, two CMUT cells are disposed at one intersection, and the upper electrodes of them are connected with a wiring 1001. In FIG. 11, there is shown a part of the array, which comprises the upper electrodes for four channels in the azimuth direction and the lower electrodes for three channels in the elevation direction. As for a probe used for an ultrasonic diagnostic apparatus, in the case of a general linear probe, for example, upper electrodes for 192 channels are disposed.

This embodiment 2 is characterized in that the CMUT cells disposed in the elevation direction above the lower electrodes have different disposition patterns of the projections 206 of the insulating film with respect to each lower electrode, as shown in FIG. 11.

In the case of a transducer having such a plurality of lower electrodes disposed in the elevation direction as shown in FIG. 11, a form and intensity of ultrasonic beam transmitted and received at each intersection of the upper electrode and the lower electrode can be controlled by changing the voltage applied to each lower electrode, and thereby improvement in image quality of diagnostic images can be expected. Therefore, the voltage applied to the upper and lower electrodes at the time of driving the CMUT changes according to the voltage applied to each lower electrode, and projections of the insulating film in the CMUT cell can be disposed on each lower electrode according to the magnitude of the applied voltage. Positions at which the projections are disposed and number of projections to be disposed can be determined according to the method for disposing the projections explained for the embodiment 1 described above.

In the transducer shown in FIG. 11, in order to make the beam width for the elevation direction narrow, a larger voltage is applied to the lower electrode 2022 locating at the center, and a smaller voltage is applied to the lower electrodes 2021 and 2023. Therefore, seven projections are disposed in each CMUT cell overlapping with the lower electrode 2022, and five projections are disposed in each CMUT cell overlapping with the lower electrode 2021 or 2023. With such a configuration, the necessary minimum number of the projections can be disposed, and therefore even when the electrode is disposed so that it does not overlap with the projection of the insulating film as seen from above, decrease in receiving sensitivity resulting from unduly small overlapping area of the upper and lower electrodes can be suppressed.

<Configuration of Ultrasonic Diagnostic Apparatus>

Figure 12:
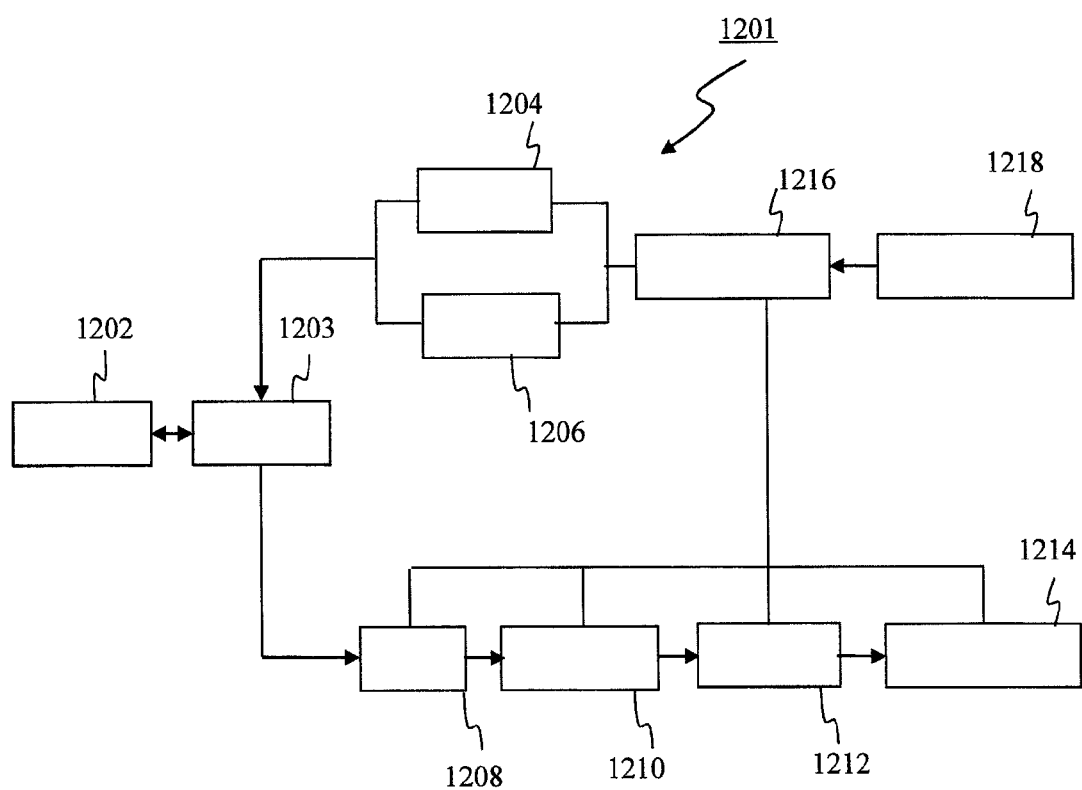
FIG. 12 is a configurational diagram of the ultrasonic diagnostic apparatus of the present invention.

Finally, the configuration of the ultrasonic diagnostic apparatus to which the present invention is applied will be explained with reference to FIG. 12. FIG. 12 is a configurational diagram of the ultrasonic diagnostic apparatus.

The ultrasonic diagnostic apparatus 1201 consists of an ultrasonic probe 1202, a transmission and reception separation part 1203, a transmitting part 1204, a bias part 1206, a receiving part 1208, a phasing addition part 1210, an image processing part 1212, a display part 1214, a control part 1216, and an operation part 1218.

The ultrasonic probe 1202 is a device for transmitting and receiving ultrasonic waves to and from a subject by being contacted with the subject, and it is provided with an array of ultrasonic transducer elements on a surface to be contacted with the subject. As the ultrasonic transducers, the ultrasonic transducer of the present invention is employed. An ultrasonic wave is transmitted from the ultrasonic probe 1202 to the subject, and reflected echo signals from the subject are received by the ultrasonic probe 1202. The transmitting part 1204 and the bias part 1206 are devices for supplying a driving signal to the ultrasonic probe 1202.

The receiving part 1208 is a device for receiving the reflected echo signals outputted from the ultrasonic probe 1202. The receiving part 1208 performs processing of the received reflected echo signals such as analog-to-digital conversion.

The transmission and reception separation part 1203 switches and separates transmission and reception, so that a driving signal is sent from the transmitting part 1204 to the ultrasonic probe 1202 at the time of transmission, and a received signal is sent from the ultrasonic probe 1202 to the receiving part 1208 at the time of reception.

The phasing addition part 1210 is a device for performing phasing addition of the received reflected echo signals.

The image processing part 1212 is a device for constituting a diagnostic image (for example, tomogram or blood flow image) on the basis of the reflected echo signals subjected to the phasing addition.

The display part 1214 is a display for displaying the diagnostic image obtained by image processing.

The control part 1216 is a device for controlling the constituent elements mentioned above.

The operation part 1218 is a device for giving directions to the control part 1216. The operation part 1218 is, for example, an inputting means such as trackball, keyboard and mouse.

The ultrasonic diagnostic apparatus of the present invention is characterized by using an ultrasonic transducer comprising a minimum number of necessary projections optimally disposed between the upper and lower electrodes as an ultrasonic transducer of an ultrasonic probe, and provides effects of preventing decrease in effectual electric field produced by driving voltage, improving transmission and reception sensitivity, and so forth.

INDUSTRIAL APPLICABILITY

The ultrasonic transducer and ultrasonic diagnostic apparatus of the present invention can be widely used as an apparatus for medical diagnosis or diagnosis of structures.

DESCRIPTION OF NUMERICAL NOTATIONS 101, 202, 2021, 2022, 2023 . . . Lower electrode
102, 204 . . . Hollow part
103, 201, 209, 210 . . . Insulating film
200 . . . Semiconductor substrate
203 . . . Lower insulating film
205 . . . Upper insulating film
104, 207 . . . Upper electrode
105 . . . Membrane
106 . . . Lower surface of membrane
107, 214 . . . Lower surface of hollow part
108 . . . First projection at the center of membrane
109 . . . n-th projection of insulating film
110 . . . (n+2)th projection of insulating film
111 . . . (n+4)th projection of insulating film
206, 2061, 2062, 2063, 6061, 6062, 6063, 6064 . . . Projection of insulating film
208 . . . Opening of upper electrode
211 . . . Wet etching hole
212 . . . Opening reaching lower electrode
213 . . . Opening reaching upper electrode
215 . . . Lower surface of membrane except for lower surface of projection
401 . . . Contacting point of lower surface of membrane and lower surface of hollow part
1001 . . . Wiring connecting upper electrodes
1101 . . . CMUT chip
1201 . . . Ultrasonic diagnostic apparatus
1202 . . . Ultrasonic probe
1203 . . . Transmission and reception separation part
1204 . . . Transmitting part
1206 . . . Bias part
1208 . . . Receiving part
1210 . . . Phasing addition part
1212 . . . Image processing part
1214 . . . Display part
1216 . . . Control part
1218 . . . Operation part

The invention claimed is:

1. An ultrasonic transducer comprising:
a first electrode;
a lower insulating film formed on the first electrode;
an upper insulating film provided so as to form a hollow part above the lower insulating film;
a second electrode formed on the upper insulating film wherein:
the lower insulating film or the upper insulating film has a plurality of projections formed on a side of the hollow part, and
the first electrode or the second electrode has openings formed at positions corresponding to the positions at which the plurality of projections are formed;
a first projection of the plurality of projections is formed on the upper insulating film or the lower insulating film at a position corresponding to at least a center of a membrane comprising the upper insulating film and the second electrode;
a second projection of the plurality of projections is formed between the first projection and an edge of the hollow part; and
a third projection of the plurality of projections is formed between the second projection and the edge of the hollow part; and
provided that the first projection is contacted with the upper insulating film or the lower insulating film, and a part of the membrane on a straight line connecting the first projection and the edge of the hollow part is contacted with the lower insulating film by driving voltage applied to the first electrode and the second electrode, the second projection is formed on the contacting part of the membrane.

2. The ultrasonic transducer according to claim 1, wherein:
provided that a part of the membrane on a straight line connecting the second projection and the edge of the hollow part is contacted with the lower insulating film by driving voltage applied to the first electrode and the second electrode, the third projection is formed on the contacting part of the membrane.

3. The ultrasonic transducer according to claim 1, wherein:
provided that the membrane is contacted with the lower insulating film between the first projection and the second projection by driving voltage applied to the first electrode and the second electrode, the third projection is formed at the middle point between the first projection and the second projection.

4. The ultrasonic transducer according to claim 1, wherein:
ultrasonic transducers are disposed in an array, and the ultrasonic transducers have different disposition patterns of projections.

5. A transducer array comprising a plurality of disposed ultrasonic transducers, wherein each of the ultrasonic transducers is the ultrasonic transducer according to claim 1.

6. The transducer array according to claim 5, wherein:
the ultrasonic transducer have different disposition patterns of projections.

7. The transducer array according to claim 6, wherein:
the ultrasonic transducers are disposed along mutually perpendicular two-dimensional directions, and
the ultrasonic transducers disposed along one of the directions have different disposition patterns of projections.

8. An ultrasonic diagnostic apparatus comprising:
an ultrasonic probe for transmitting and receiving ultrasonic waves to or from a subject;
an image processing part for constituting an ultrasonogram on the basis of received ultrasonic signals outputted from the ultrasonic probe; and
a display part for displaying the ultrasonogram;
wherein:
the ultrasonic probe comprises:
an ultrasonic transducer comprising a first electrode,
a lower insulating film formed on the first electrode,
an upper insulating film provided so as to form a hollow part above the lower insulating film, and
a second electrode formed on the upper insulating film,
wherein the lower insulating film or the upper insulating film has a plurality of projections formed on the side of the hollow part, and the first electrode or the second electrode has openings formed at positions corresponding to the positions at which the plurality of projections are formed.

9. The ultrasonic diagnostic apparatus according to claim 8, wherein:
the ultrasonic transducers has a first projection of the plurality of projections formed on the upper insulating film or the lower insulating film at a position corresponding to at least the center of a membrane comprising the upper insulating film and the second electrode.

10. The ultrasonic diagnostic apparatus according to claim 9, wherein:
the ultrasonic transducer has a second projection of the plurality of projections formed between the first projection and an edge of the hollow part; and
provided that the first projection is contacted with the upper insulating film or the lower insulating film, and a part of the membrane on a straight line connecting the first projection and the edge of the hollow part is contacted with the lower insulating film by driving voltage applied to the first electrode and the second electrode, the second projection is formed on the contacting part of the membrane.

11. The ultrasonic diagnostic apparatus according to claim 10, wherein the ultrasonic transducer has a third projection of the plurality of projections formed between the second projection and the edge of the hollow part; and
provided that a part of the membrane on a straight line connecting the second projection and the edge of the hollow part is contacted with the lower insulating film by driving voltage applied to the first electrode and the second electrode, the third projection is formed on the contacting part of the membrane.

12. The ultrasonic diagnostic apparatus according to claim 10, wherein:
the ultrasonic transducer has a third projection of the plurality of projections formed between the second projection and the edge of the hollow part; and
provided that a part of the membrane on the straight line connecting the second projection and the edge of the hollow part is contacted with the lower insulating film by driving voltage applied to the first electrode and the second electrode, the third projection is formed at a position shifted to the first projection side from the contacting part of the membrane.

13. The ultrasonic diagnostic apparatus according to claim 10, wherein:
the ultrasonic transducer has a third projection of the plurality of projections; and
provided that the membrane is contacted with the lower insulating film between the first projection and the second projection by driving voltage applied to the first electrode and the second electrode, the third projection is further formed at the middle point between the first projection and the second projection.

14. The ultrasonic diagnostic apparatus according to claim 8, which uses:
an ultrasonic transducer comprising the ultrasonic transducers disposed in an array, wherein each ultrasonic transducer has different disposition pattern of projections.

15. The ultrasonic transducer according to claim 1, wherein the third projection is a different length from at least one of the first and second projection.

* * * * *